United States Patent [19]
Buchanan et al.

[11] Patent Number: 5,494,033
[45] Date of Patent: Feb. 27, 1996

[54] BIOMAGNETOMETER WITH SEALED VACUUM ENCLOSURE AND SOLID CONDUCTION COOLING

[75] Inventors: D. Scott Buchanan, Escondido; Laurence Warden, San Diego; Scott W. Riley, Oceanside; Richard T. Johnson, San Diego; K. Randy Brimhall, San Diego; Keith A. Esser, San Diego, all of Calif.

[73] Assignee: Biomagnetic Technologies, Inc., San Diego, Calif.

[21] Appl. No.: 80,876

[22] Filed: Jun. 21, 1993

[51] Int. Cl.⁶ .................................................. A61B 5/05
[52] U.S. Cl. .................................... 128/653.1; 324/248
[58] Field of Search ...................... 128/653.1; 324/248; 505/846

[56] References Cited

U.S. PATENT DOCUMENTS

| | | | |
|---|---|---|---|
| 4,827,217 | 5/1989 | Paulson | 324/248 |
| 4,951,674 | 8/1990 | Zanakis et al. | 128/653.1 |
| 4,996,479 | 2/1991 | Hoenig | 128/653.1 |
| 5,193,348 | 3/1993 | Schnapper | 324/248 |

*Primary Examiner*—Ruth S. Smith
*Attorney, Agent, or Firm*—Gregory Garmong

[57] ABSTRACT

A biomagnetometer includes a magnetic field sensor including a magnetic field pickup coil and a detector of small electrical currents flowing within the pickup coil. A vacuum-tight enclosure surrounds the sensor. The enclosure has a concavely upwardly curved first wall, with the magnetic field pickup coil located adjacent to the first wall. A vented reservoir of liquefied gas is located within the enclosure, and a solid thermal conductor extends from the sensor. There is a vacuum-tight thermal feedthrough by which the solid thermal conductor passes between the interior and the exterior of the enclosure. Electronic circuitry for filtering and amplifying the signals of the detector is also provided. Such a biomagnetometer is placed below the body of a reclining subject, and a second portion of the biomagnetometer can be placed above the body. In one form, the enclosures are shaped to form a cavity that receives the head of the subject therein, to achieve full head coverage of the pickup coils in the biomagnetometer.

14 Claims, 5 Drawing Sheets

BIOMAGNETOMETER WITH SEALED VACUUM ENCLOSURE AND SOLID CONDUCTION COOLING

BACKGROUND OF THE INVENTION

This invention relates to the measurement of the magnetic fields produced by a living organism and, more particularly, to a configuration for a biomagnetometer that measures such magnetic fields.

Living subjects produce biomagnetic fields as a result of bioelectric current flows in their bodies. The bioelectric current flows are produced in the brain, the heart, and the nervous system. The bioelectric current is constrained to flow within the subject's body, but the resulting biomagnetic field extends outside the body.

A biomagnetometer is an instrument that measures the biomagnetic fields that reach outside of the subject's body. The biomagnetometer can therefore measure the result of the internal electrical functioning of the body in an external, noninvasive fashion. The measured biomagnetic fields are used to infer the nature of the bioelectric current flows that produced them, which in turn are used to understand the functioning of the body in normal and abnormal circumstances.

The biomagnetometer has a biomagnetic field sensor which includes a biomagnetic field pickup coil positioned external to the body of the subject. A small electrical current flows in the pickup coil responsive to a biomagnetic field produced by the subject. The electrical current of the pickup coil is detected by a sensitive detector, preferably a Superconducting Quantum Interference Device, also known as a "SQUID". The pickup coil and the SQUID operate in the superconducting state, and are contained within a cryogenically cooled dewar during operation. Other electronics amplifies and filters the SQUID output signal, producing an output signal that is further analyzed to understand the electrical patterns of the body.

It is important to place the biomagnetic field pickup coil as closely as possible to the surface of the body of the subject, because the magnitudes of the biomagnetic fields are small to begin with, and decay rapidly with increasing distance from the subject. One of the ongoing trends in biomagnetometry has been to increase the number and spatial coverage of pickup coils around the subject, because more information can be gained by analyzing a large spatial sample of the biomagnetic field than by analyzing the output of a single pickup coil. Thus, for example, the earliest commercially available biomagnetometers had a single pickup coil, later biomagnetometers had 7 or 14 pickup coils, and current commercial biomagnetometers have 37 or more pickup coils.

The array of pickup coils is placed in a dewar that is curved to fit over the head or other portion of the body of the subject. Conventional practice has been to place the subject in a lying position with the dewar over the head of the subject. The lower end of the dewar is shaped to generally conform to the upper surface of the head.

Larger biomagnetometer arrays have been proposed arranged in the shape of a rigid helmet to cover a larger portion of the head. This approach is limited by the natural variation in head size and shape, so that a single helmet will fit only a small proportion of the population.

Recently, a biomagnetometer dewar configuration has been suggested for use with a subject in a reclining position in this "inverted" dewar design, the cryogenic reservoir is below or to the side of the subject, and the pickup coils and their enclosing dewar are below the head of the subject. This repositioning of the dewar presents some difficult problems for dewar design. In this prior proposed design, the pickup coils are cooled by a flow of low-temperature helium gas evolved from a liquid helium reservoir. The flow of helium gas is conveyed to the pickup coils through tubes.

This inverted dewar design has promise, but configurations proposed to date can be thermally inefficient and difficult to implement due to the sealing requirements of the system and the difficulty in conveying a flow of cryogenic gas through a small-diameter tube over distances on the order of a meter or more. There is a need for an improved inverted dewar that circumvents these problems. The present invention fulfills this need, and further provides related advantages.

SUMMARY OF THE INVENTION

The present invention provides a biomagnetometer having a vacuum enclosure below the body of the subject and a concavely curved surface, preferably a concavely upwardly curved surface to fit against the underside of the body of the subject. The design is thermally efficient and overcomes the practical problems of prior inverted dewars by utilizing a different cooling system than in prior designs. This configuration permits increased sensor coverage of the body by allowing one array of pickup coils to be positioned below the body of the subject and another array to be positioned above the body of the subject, with the patient in a reclining position. Greatly increased head coverage by the sensor array may thereby be achieved with the patient in a reclining position, an important advantage because the patient may not be physically or comfortably able to remain in a sitting position for lengthy periods. The apparatus also is operable with a wide variety of head shapes and sizes.

In accordance with the invention, a biomagnetometer comprises a magnetic field sensor including a magnetic field pickup coil, and an electrical current detector in electrical communication with the pickup coil. There is a vented reservoir of liquefied gas. A solid thermal conductor extends from the magnetic field sensor to the interior of the reservoir, and a vacuum-tight thermal feedthrough allows the solid thermal conductor to pass between the exterior and the interior of the reservoir. A vacuum-tight enclosure surrounds the magnetic field sensor, the reservoir, the solid thermal conductor, and the vacuum-tight thermal feedthrough. The enclosure has a wall including a first wall portion with the magnetic field pickup coil located adjacent to the first wall portion. There is an electronic circuit, with at least a portion of the electronic circuit being located exterior to the enclosure. An electrical lead extends from the electrical current detector to the portion of the electronic circuit located exterior to the enclosure, and a vacuum-tight electrical feedthrough passes the electrical lead between the interior and the exterior of the enclosure.

Stated alternatively, a biomagnetometer comprises means for sensing a magnetic field, the means for sensing including an array of magnetic field pickup coils and an array of detectors of small electrical currents flowing in the respective pickup coils. A vacuum-tight enclosure surrounds the means for sensing. A vented reservoir of cryogenic liquid is located within the enclosure, and a solid thermal conductor extends from the means for sensing to the reservoir. A vacuum-tight thermal feedthrough for the solid thermal conductor extends through a wall of the reservoir.

For use below the subject, the first wall of the enclosure is concavely upwardly curved. In an extension of this design, the biomagnetometer may further include a second enclosure having a concavely downwardly curved second wall, and a second magnetic field sensor. The second magnetic field sensor includes a second magnetic field pickup coil located within the second enclosure adjacent to the curved second wall, and a second electrical current detector in electrical communication with the second pickup coil. There is a means for cooling the second magnetic field sensor. This biomagnetometer can form a cavity between the first wall of the first enclosure and the second wall of the second enclosure, into which the head of the subject fits with the patient in a reclining position.

Thus, more generally, a biomagnetometer comprises a first dewar assembly with a vacuum-tight first enclosure having a concavely upwardly curved first wall, a first pickup coil within the first enclosure located adjacent the concavely upwardly curved first wall, a first detector of an electrical current flowing in the first pickup coil, and means for cooling the first pickup coil and the first detector. A second dewar assembly comprises a vacuum-tight second enclosure having a concavely downwardly curved second wall, a second pickup coil within the second enclosure located adjacent the concavely downwardly curved second wall, a second detector of an electrical current flowing in the second pickup coil, and means for cooling the second pickup coil and the second detector.

The biomagnetometer of the invention overcomes operating difficulties of prior inverted dewar designs by placing the magnetic field sensor in a vacuum enclosure. The magnetic field sensor is cooled by conduction along a solid conductor that reaches from the magnetic field sensor, to the reservoir of cryogenic fluid, and through the wall of the reservoir via the vacuum feedthrough. There is no gas flow around the pickup coils and other portions of the magnetic field sensor that would increase the heat flow to the magnetic field sensor, thereby improving the thermal stability and efficiency of the system.

As a result of this design improvement, a "clamshell" vacuum enclosure design with a first vacuum enclosure below the reclining subject and a second vacuum enclosure above the subject becomes practical. Sensor coverage adaptable to various head shapes and sizes is thence available around the entire periphery of the body, and in particular around the entire periphery of the head. Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 3 is a side sectional view of a first embodiment of the feedthrough of the invention at various stages of its assembly, showing in FIG. 3(a) the components prior to assembly, in FIG. 3(b) the partially assembled feedthrough, and in FIG. 3(c) the completed feedthrough;

FIG. 8 is a schematic view of another embodiment of the biomagnetometer of the invention, showing in FIG. 8(a) an end view and in FIG. 8(b) a side view.

DETAILED DESCRIPTION OF THE INVENTION

Figure 1:
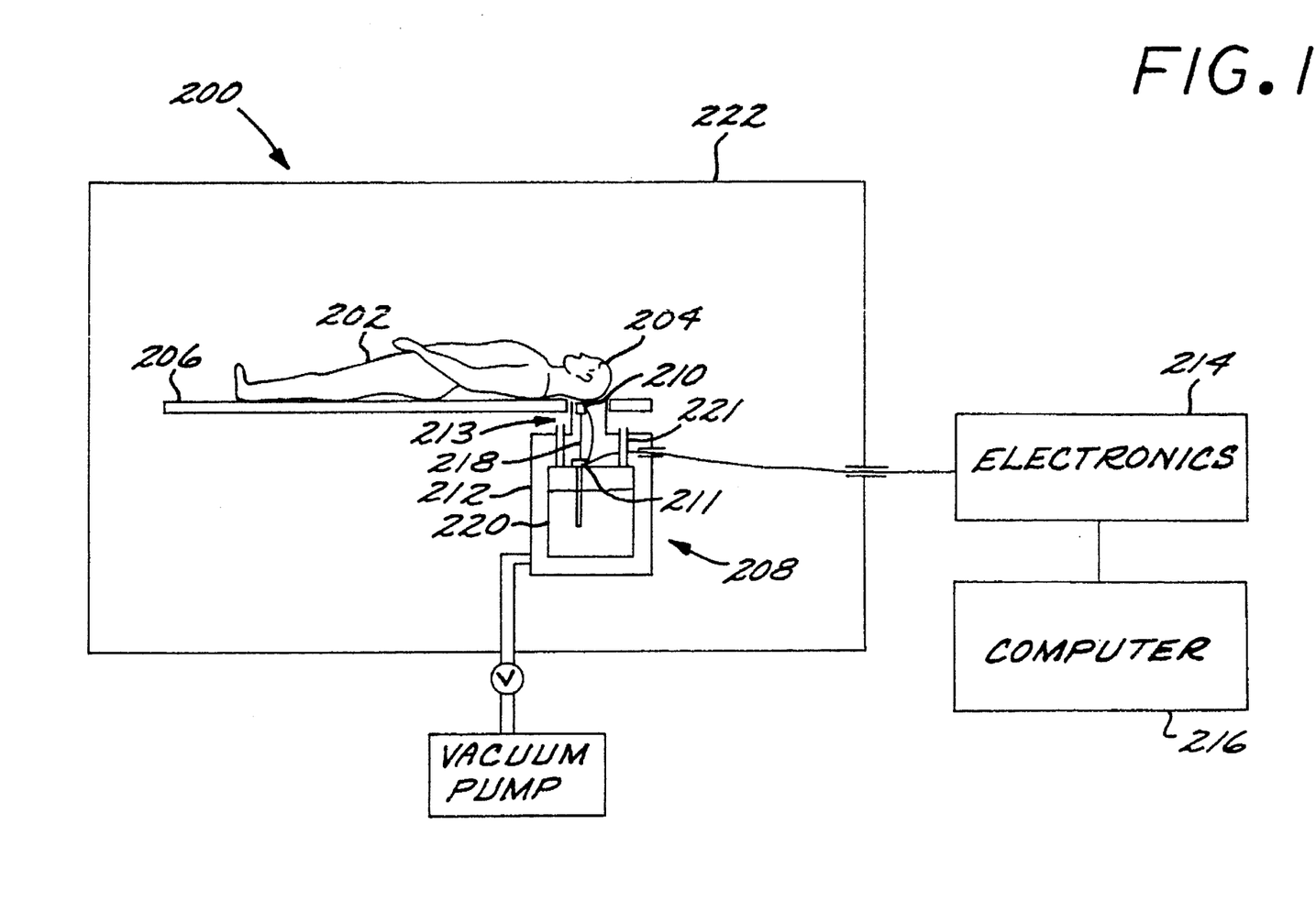
FIG. 1 is a schematic side elevational view of a biomagnetometer according to the invention.

As illustrated in FIG. 1, the present invention is preferably embodied in an apparatus 200 for obtaining biomagnetic data from a body 202 of a human patient or subject. More specifically, the data are often obtained from bioelectromagnetic sources within the head 204 of the subject. The subject reclines upon a table 206 in proximity to a biomagnetometer 208. The biomagnetometer 208 includes an array of a first plurality of magnetic field pickup coils 210 for measuring small magnetic fields. The pickup coils may be magnetometers or gradiometers, or of other configuration as may be appropriate for a particular application. The geometry of the array of magnetic field pickup coils may be curved to cover one-half of the head, in the shape of a helmet to surround most of the head, or other geometry as needed for particular applications.

In each operating sensor channel, the output signal of the magnetic field pickup coil 210 is detected by a detector, preferably a superconducting quantum interference device 211 ("SQUID"). The pickup coil 210 and its associated SQUID detector 211 are collectively termed a "magnetic field sensor" 213. Both the magnetic field pickup coil 210 and the SQUID 211 are maintained at a cryogenic operating temperature and in a vacuum within a vacuum enclosure 212. In the preferred practice a large number of sensing coils 210 and SQUIDs 211 are located in one vacuum enclosure 212, or multiple vacuum enclosures may be used. The vacuum enclosure is evacuated by a vacuum pump.

The electronics arrangement of the biomagnetometer 208 is illustrated schematically in FIG. 1. The magnetic signals from the brain are picked up by the magnetic field pickup coil 210 in the vacuum enclosure 212, which produces a small electrical current output signal when penetrated by a magnetic flux. The output signal of the pickup coil 210 is detected by a detector, in this case the SQUID 211. The SQUID 211 produces an electrical voltage proportional to the magnetic flux detected by the pickup coil. The output signal of the SQUID 211 is processed in an ambient-temperature electronic signal processor 214, which typically includes balancing, gain, amplifying, and filtering circuitry, and stored and analyzed in a computer 216 as a function of time. Each sensor channel results in a record of its response to the magnetic field produced by all of the sources within the subject brain, as those sources act simultaneously on the pickup coil of the sensor channel. FIG. 1 depicts a single sensor channel including a pickup coil and a SQUID. In practice, there are usually multiple such sensor channels in the vacuum enclosure 212.

The magnetic field sensor 213 is cooled by removal of heat via a solid thermal conductor 218. The thermal conductor 218 extends from the magnetic field sensor components to be cooled within the interior of the vacuum enclosure 212, principally the pickup coil 210 and the SQUID 211, to a thermal sink here illustrated as a vented reservoir 220 of a cryogenic fluid. The solid thermal conductor is a solid conductor of heat, preferably made of copper, a copper alloy, aluminum, an aluminum alloy, silver, a silver alloy, gold, or a gold alloy. It permits heat to flow from the magnetic field sensor 213 to the reservoir 220, across the wall of the reservoir 220, and to the cryogenic fluid within the reservoir. The reservoir 220 is supported from the wall of the vacuum enclosure 212 by upwardly extending hollow tubular supports 221. These supports 221 also serve as vents and fill tubes for the interior of the reservoir 220.

The biomagnetometer 208 and the body 202 of the subject are preferably, but not necessarily, enclosed within a magnetically shielded room 222, also termed an MSR, that shields the apparatus and magnetic field source from external influences. By screening off the external influences, the amount of signal processing and filtering required to obtain a meaningful indication of the biomagnetic field are reduced. The electronics 214 and computer 216 are typically located outside the MSR 222, so that they do not interfere with the sensing of the magnetic field of the subject.

The basic structure of some components of this system are known. The construction of vacuum enclosures disclosed in U.S. Pat. No. 4,773,952. The construction and operation of magnetic field sensors, including pickup coils, SQUIDs, and ambient-temperature SQUID electronics are disclosed in U.S. Pat. Nos. 3,980,076; 4,079,730; 4,386,361; and 4,403,189. A biomagnetometer is disclosed in U.S. Pat. No. 4,793,355. Magnetically shielded rooms are disclosed in U.S. Pat. No. 3,557,777 and 5,043,529. The disclosures of all of these patents are incorporated herein by reference.

Figure 2:
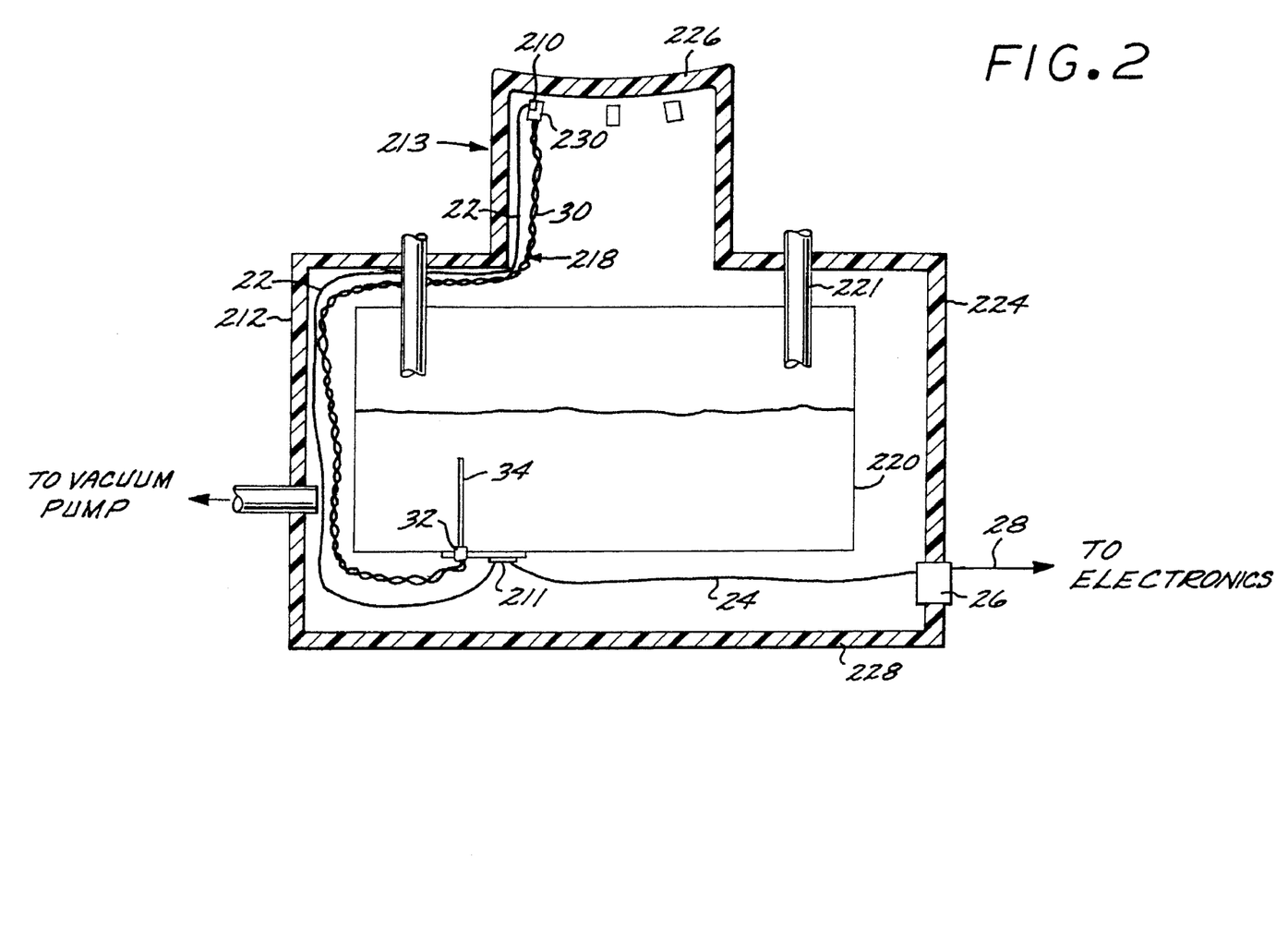
FIG. 2 is a schematic side sectional view of the vacuum enclosure of the biomagnetometer and the cryogenic reservoir.

FIG. 2 depicts the vacuum enclosure 212 in greater detail. A wall 224 of the vacuum enclosure forms a sealed enclosure. In operation, the inside of the vacuum enclosure 212 is evacuated, so that a one-atmosphere pressure differential exists across the walls of the vacuum enclosure 212. The wall 224 includes a first wall 226 and a second wall 228. A support 230 for the pickup coil 210 is positioned in the interior of the vacuum enclosure 212, as closely as possible to the first wall 226 and positioned to hold the pickup coil in the de sired orientation. In the preferred case, there are multiple sets of pickup coils 210 and SQUIDs 211, but the details of the external connections are illustrated for only one.

As shown in FIG. 1, the vacuum enclosure 212 is placed below the body 202 of the subject. The first wall 226 is desirably concavely upwardly curved to generally match the curvature presented by the portion of the body of the subject under examination. (More generally, the first wall is concavely outwardly curved to fit against some portion of the body.) In the preferred and illustrated case, the biomagnetometer is positioned to detect signals arising from the brain of the subject. The first wall 225 is therefore positioned as closely as possible below the head 204 of the reclining subject, and the curvature of the first wall 225 is generally selected to conform to the curvature of the head 204 of the subject. When multiple pickup coils 210 are used, this curvature permits them to be closely positioned around the surface of the head of the subject, in a quasi-helmet fashion for a portion of the head.

In the preferred embodiment, the SQUID 211 is mounted on the bottom of the reservoir 220. The pickup coil 210 communicates with the SQUID 211 by an electrical lead 22. The SQUID 211 communicates electrically with the exterior of the vacuum enclosure 212 by electrical leads. An internal electrical lead 24 extends from the SQUID 211 to an electrical feedthrough 25 of conventional design, placed in the wall of the vacuum enclosure 212. Electrical vacuum feedthroughs 26 are available commercially from suppliers such as Cannon. An external electrical lead 28 extends from the electrical feedthrough 26 to the external electronics 214.

The magnetic field sensor 219, including the support 290, the pickup coil 210, and the SQUID 211 must be cooled to a cryogenic temperature to be operable. When a patient is in a sitting position, nearly full head coverage of the array of pickup coils may be achieved by using one large, contoured vacuum enclosure having a helmet-configured end. This approach is not readily adaptable to a wide range of head sizes and shapes, however. Alternatively, and more practically, two vacuum enclosures can be used, one positioned on each side of the head, to achieve full-head coverage. Even then, however, many patients who require biomagnetic studies cannot sit for extended periods, and therefore the patient must be in a reclining position as the studies are performed.

For a subject in a reclining position, full head coverage can be obtained by placing one vacuum enclosure above the head and one below the head, in an alternative embodiment of the invention (to be later discussed in relation to FIG. 7). A vacuum enclosure containing sensors that is to be placed above the head can be of conventional design, but placement of the vacuum enclosure below the head presents some design challenges in cooling the sensors to cryogenic temperatures. The cooling of the sensors in such an inverted vacuum enclosure design has been addressed in one context in European Patent Application No. 89116922.2, which discloses the cooling of the pickup coils and SQUIDs by a flow of cryogenic gas evaporated from the cryogenic coolant reservoir and conducted to the pickup coils and SQUIDs through tubes. However, conducting of cryogenic gases through tubes is difficult and inefficient, and it may be awkward to place the cooling tubes properly within the somewhat-confined space of the vacuum enclosure when there are multiple sensors to be cooled. Such tubes may plug. Maintaining thermal stability is difficult in the presence of a relatively high gas flow, leading to increased noise of the system. The gas flow approach also consumes a large amount of helium.

An alternative is to use a sealed system. However, the cooling to cryogenic temperature of the pickup coils and SQUIDs located within such a hermetically sealed structure, using a liquefied cryogenic fluid as the coolant, is difficult to achieve. The approach of the European Patent Application No. 89116322.2 would not be operable in this case, because the coolant gas would be exhausted to the interior of the vacuum enclosure to provide cooling, negating the thermal insulation effect of the vacuum.

In the preferred design approach of the present invention, the coolant sink is the reservoir 220 located within the vacuum enclosure 212 and typically at least 20–30 centimeters or more from the pickup coils 210 that are to be cooled to nearly absolute zero. Heat must be transferred from the pickup coils 210 and their support 230, the SQUID 211, and the wires 22 located within the vacuum of the vacuum enclosure 212, through the walls of the reservoir 220 and to the cryogenic reservoir 220.

In the preferred embodiment, to accomplish this thermal transfer, a portion of the solid thermal conductor 218, termed the solid thermal conductor 30, extends from the support 230 to a solid thermal feedthrough 32, placed in the wall of the reservoir 220. After passing through the feedthrough 32, a portion of the solid thermal conductor 218, termed the solid thermal conductor 34, extends into the interior of the cryogenic reservoir 220 and thence to a cryogenic fluid therein. The solid thermal conductor 218 may be formed of single metallic conductor or multiple metallic conductor elements such as braided wires. Together, the solid thermal conductors 30 and 34 constitute the solid thermal conductor 218 discussed more generally in relation to FIG. 1.

The thermal feedthrough 32 must have a high efficiency in conducting heat across and through the wall of the reservoir 220, and at the same time resist gas leaks from the interior of the reservoir 220 into the interior of the vacuum enclosure 212. Portions of the thermal feedthrough 32 are cooled to near-cryogenic temperature during operation. The thermal feedthrough 32 may be cycled between low and ambient temperature many times in its service life. When a structure formed of several different materials is cooled in this manner, thermal strains and displacements develop as a result of the differences in thermal expansion coefficients of the materials of construction. Significant thermal displacements may cause structural failures even in conventional structures, but in a vacuum-sealed structure even a minor internal failure of the feedthrough can result in a gas leak. The problem is intensified where the structure is repeatedly heated and cooled, leading to thermal fatigue of the structure. The design of the thermal feedthrough provides a significant challenge, and three different designs have been developed for use in the present invention.

Figure 3A:
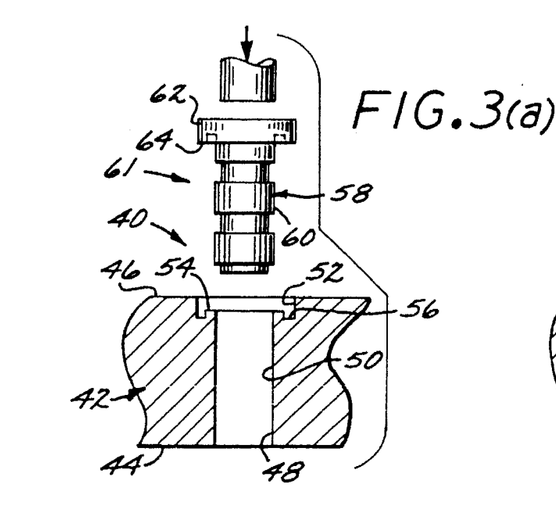
Figures 3B, 3C:
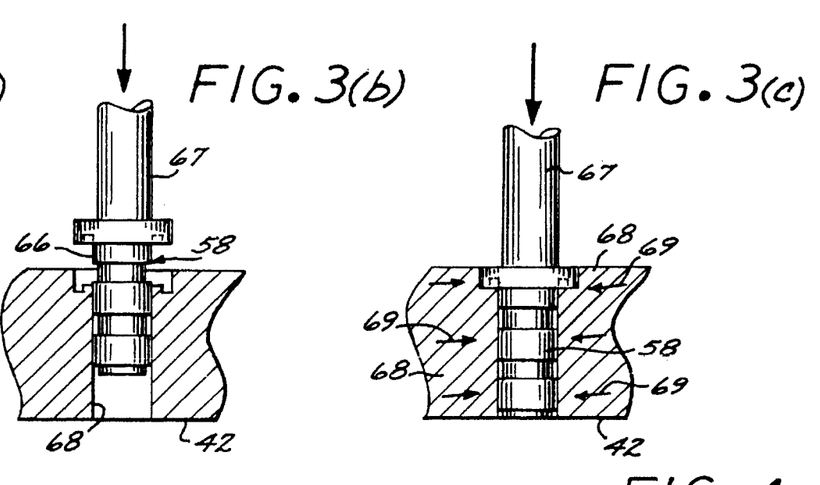
Figure 4:
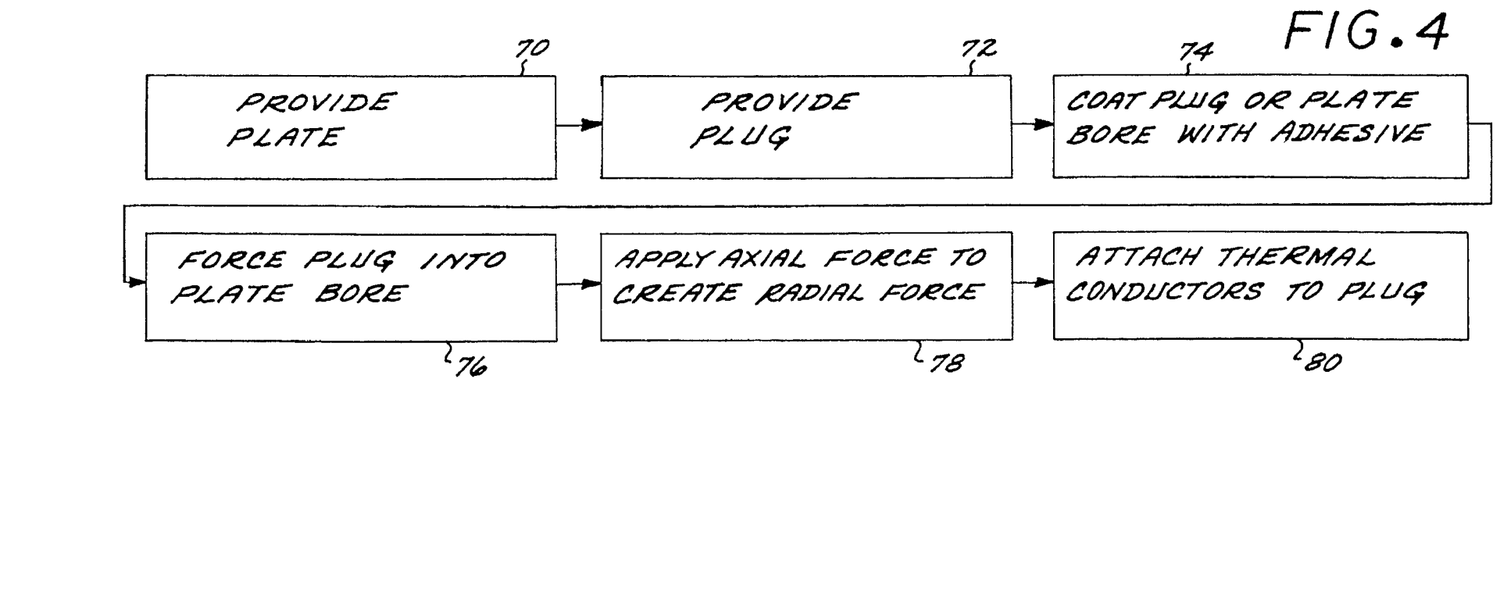
FIG. 4 is a process flow diagram for a method of preparing the first embodiment of the feedthrough.

FIG. 3 depicts a first embodiment of the thermal feedthrough of the invention, and FIG. 4 illustrates the assembly of the feedthrough. Referring in particular to FIG. 3(a), a feedthrough 40 includes a plate 42 made of a nonmagnetic material, preferably a fiber-reinforced plastic material such as fiberglass. The plate 42 has a first surface 44 and a second surface 46. The size of the plate 42 is not critical, provided that the plate has sufficient strength that it does not deform significantly under the one-atmosphere pressure differential. By way of illustration and not of limitation, a preferred plate 42 is about 3 centimeters thick and about 43 centimeters in diameter.

A cylindrically symmetric bore 48 extends through the thickness of the plate 42 from the first surface 44 to the second surface 45. The bore 48 has two portions along its length, a first portion 50 adjacent to the first surface 44 and a second portion 52 adjacent to the second surface 46. The first portion 50 has a first diameter and the second portion 52 has a second, larger diameter. A shoulder 54 lies between the first portion 50 and the second portion 52.

In a preferred embodiment, a reentrant recess 56 is positioned around the diameter of the second portion 52 of the bore, at a location where the second portion 52 contacts the shoulder 54. The recess 56 is in the form of a toroidal cutout portion or notch extending from the diameter of the second portion 52 to a diameter somewhat greater than the diameter of the first portion 50. By way of illustration and not limitation, in a preferred embodiment, the first portion 50 has a length of 2.84 centimeters and a diameter of 0.95 centimeters, and the second portion 52 has a length of 0.47 centimeters and a diameter of 1.58 centimeters. The recess 56 has a length of 0.15 centimeters.

A cylindrically symmetric plug 58 is sized to fit within the bore 48 of the plate 42. The plug is preferably made of substantially pure copper, a copper alloy, substantially pure aluminum, an aluminum alloy, substantially pure silver, a silver alloy, substantially pure gold, or a gold alloy. These metals all have acceptable thermal conductivity, with the pure metals being preferred and pure copper being most preferred.

The plug 58 has a first portion 60 with a maximum diameter sized to achieve an interference fit with the first portion 50 of the bore of the plate 42. The first portion 60 of the plug 58 may have a smooth outer diameter, or may have a stepped outer diameter, as shown. The stepped outer diameter configuration is preferred, as it aids in achieving a good seal of the plug 58 to the plate 42 and also eases the assembly operation. The plug 58 has a second portion 62 sized to achieve a slip fit with the second portion 52 of the bore of the plate 42. The interference fit is typically achieved by sizing the outer diameter of the first portion 60 of the plug 58 to be about 0.05 millimeters larger than the inner diameter of the respective portion of the plate 42, within available machining tolerances. Even though the plug is of slightly larger diameter than the bore, the assembly is achieved by force fitting the plug into the bore because the plug is made of a slightly compliant material.

The second portion 62 of the plug 58 has a lip 64 extending therefrom parallel to the cylindrical axis of the plug 58. The lip 64 is configured and sized to fit within the reentrant recess 56 of the second portion 52 of the bore 48 of the plate 42, with a gap of about 0.05 millimeters to allow excess adhesive to be expelled during assembly.

FIGS. 3(b) and 3(c) present the physical arrangement of the components during the stages of assembly. Referring to FIGS. S(b) and 4, to assemble the feedthrough 40, the plate 42 is provided, numeral 70, and the plug 58 is provided, numeral 72. Immediately before assembly, the first and second portions of the bore 48, and/or the first and second portions of the plug 58 are coated with an adhesive 66, numeral 74. The adhesive 66 is preferably a curable adhesive such as an epoxy. An acceptable epoxy is Model 810, made by Crest. This epoxy cures at ambient temperature in a time of about 4 days after application, permitting the mechanical assembly to be completed before the epoxy hardens. The plug 58 is inserted into the bore 48 and forced downwardly against the interference fit using a tool 67 that fits against the end of the plug 58, numeral 76.

At full insertion, the plug 58 bottoms against the shoulder 54 and the lip 54 engages the reentrant recess 55. At this point, the compressive force on the tool 67 is increased to at least about 6000 pounds for at least about 80 seconds, numeral 78. This compressive force on the tool 67 causes the material in area 52 of plug 58 to flow radially outwardly into the plate 42, in a region 68 adjacent to the first portion 52 of the bore 48. The compressive force is great enough that a 0.25–0.88 millimeter impression is left in the plug after the compression tool is removed. A residual radially inwardly directed compressive force remains in the region 68, as indicated by the arrows 69 in FIG. 3(c).

Finally, the thermal conductors 80 and 34 are affixed to the opposite ends of the plug 58, numeral 80. The preferred approach to attaching the thermal conductors 30 and 34 is clamped connections using screws or bolts. Alternatively, the conductors can be hard soldered prior to assembly, as long as they are configured so that there is room to use the tool 67.

In the most demanding type of application, a vacuum is drawn on one side of the plate 42 (e.g., the interior of the vacuum enclosure 212 of FIGS. 1 and 2). The close fit between the plug 58 and the bore 48 of the plate 42, the presence of the epoxy adhesive 66, and the radially inward compressive force 69 all cooperate to establish a vacuum-tight, hermetic seal so that gas cannot leak through the feedthrough 40 from the external environment into the interior of tile vessel. In service, the external thermal conductor 34 is cooled to cryogenic temperature by contact with a heat sink. Heat flows from the sensor 213 along the internal thermal conductor 30, through the plug 58, along the external thermal conductor 34, and to the heat sink. The plug 58 and the adjacent portions of the plate 42 are cooled to cryogenic temperatures. The metallic plug 58 has a smaller thermal expansion coefficient than the fiber-reinforced plastic plate 42. In the cooling process, the plug 58 has a natural tendency to contract radially less than the plate 42 at the bore 48. It is important to cool the assembly of plug and plate slowly to prevent the plug from pulling away from the plate. The epoxy adhesive has some compliance and so continues to act as a sealant between the plug and the plate, opposing the tendency for a leak path to open between the plug 58 and the bore 48, so that there is a tendency for a leak path to open between the plug 58 and the bore 48. The epoxy adhesive has some compliancy to prevent such a leak. The radial relaxation of the residual compressive force 69 in the plate 42 also serves to maintain the bore 48 in close contact with the plug 58, also resisting the tendency to form a leak path.

Ten feedthroughs 40 were prepared in a single plate by the approach just described. The plate and feedthroughs were cycled between ambient temperature and a temperature of 4K for a total of 12 cycles to test the structure. There were no failures.

Figure 5:
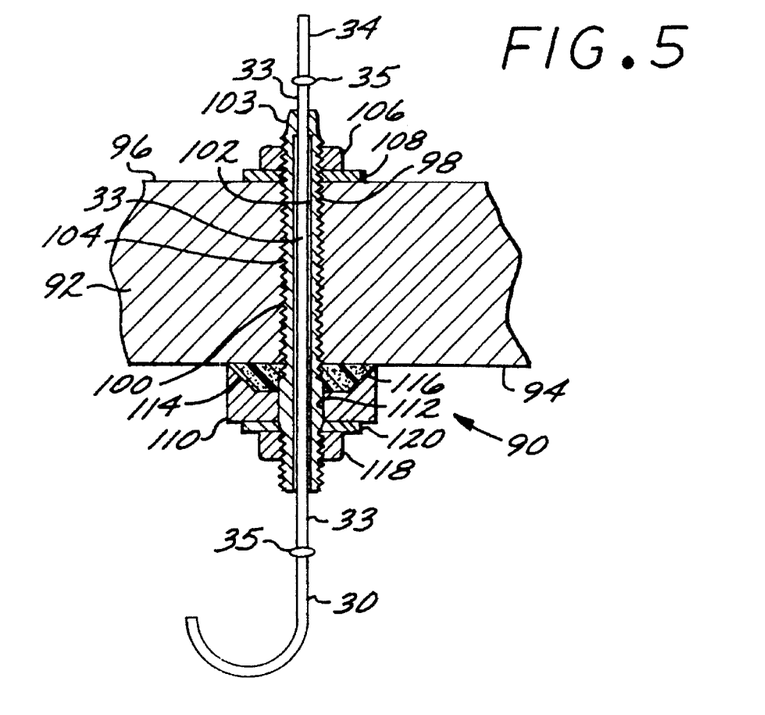
FIG. 5 is a side sectional view of a second embodiment of a thermal feedthrough.

A second embodiment of the feedthrough is shown in FIG. 5. A feedthrough 90 includes a fiber-reinforced plastic plate 92, which is preferably of the same material as the plate 42 described previously. The plate has a first surface 94 and a second surface 96. The plate 92 has a bore 98 therethrough extending between the surfaces 94 and 96. The bore 98 is of substantially constant diameter and is internally threaded.

A bolt 100 is externally threaded with threads to engage the threads of the bore 98. The bolt 100 is made of a metallic material such as a copper-beryllium alloy, most preferably an alloy of copper and about 2 weight percent beryllium. This alloy has a lower thermal conductivity than pure copper, but has higher strength. The higher strength is beneficial in sustaining the axial mechanical loadings present in the bolt 100 that are not imposed upon the plug 58 in the embodiment of FIG. 3.

The bolt 100 is of sufficient length to extend between the surfaces 94 and 95, and a short distance beyond on each side. The bolt 100 has an interior bolt bore 102 of a first diameter extending through the interior of the bolt 100, of sufficient length to extend along most of the length of the bolt 100, and a second bore 103 of a small diameter than the first diameter extending along the balance of the length of the bolt 109. The bolt bores 102 and 103 reduce the effective radial and longitudinal thermal expansion forces of the bolt 100 when the feedthrough 90 is cooled during service, adding in the avoidance of a leak path through the feedthrough 90. A metallic conductor 33 of high thermal conductivity is sealed into the bolt at the bolt bore 103, preferably by hard soldering.

An adhesive layer 104 is present between the bolt 100 and the plate bore 98. The adhesive is preferably the same type of epoxy used as the adhesive 66.

A first retainer, preferably a nut 106, 1s threaded to the end of the bolt 100 extending out of the plate 92 from its second surface 96. A nylon washer 108 is preferably placed between the nut 106 and the second surface 96.

A dam 110 made of a compliant material such as polytetrafluoroethylene (also known as teflon) is placed against the first surface 94. The dam 110 has an axial bore 112 that receives the bolt 100 therethrough. The dam 110 further has an internal cavity 114 that is filled with a flowable adhesive 116 during assembly. The flowable adhesive 116 is preferably the same material as the adhesive 104 and the adhesive 66. The dam 110 seals against the first surface 94 of the plate 92 and against the bolt 100.

A second retainer, preferably a nut 118, is threaded to the end of the bolt 100 extending out of the plate 92 from the first surface 94 and out of the dam 110. A nylon washer 120 is preferably placed between the nut 118 and the surface of the dam 110.

One of the metallic thermal conductors 30 is affixed to one end of the bolt 100, and the other of the metallic thermal conductors 34 is affixed to the other end of the bolt 100. The conductors are preferably affixed by hard soldering, such as silver soldering at joints 25, preferably before the feedthrough is assembled to the plate.

When the feedthrough 90 is assembled, the threads of the bolt 100 and/or the interior of the plate bore 98 are coated with the flowable, as-yet-uncured epoxy adhesive 104. The bolt 100 is threaded into the plate bore 98, the washer 108 is placed over the end of the bolt 100, and the nut 106 is threaded onto the bolt 100. At the other end, the cavity 114 of the dam 110 is filled with the flowable epoxy adhesive 116 and the dam 110 is placed over the end of the bolt 100. The washer 120 is placed over the end of the bolt 100, and the nut 118 is threaded onto the bolt 100.

The nut 106 is tightened slightly to seal the dam 110 to the first surface 94 and to the end of the bolt 100. The nut 106 is further tightened, and the nut 118 may also be tightened. The tightening of the nuts forces flowable epoxy adhesive 116 from the cavity 114 into any remaining space between the threads of the bolt 100 and the threaded plate bore 98. The state of compression is maintained during the curing of the epoxy adhesive. The dam 110 compresses and deforms. As a result of this process, any air pockets in the epoxy adhesive are either removed or compressed substantially during curing. The result is a vacuum-tight, hermetic seal so that gas cannot leak from one side of the plate 92 to the other during service, even after cooling and heating of the feedthrough 90.

The thermal conductors 30 and 34 are preferably attached to the ends of the bolt 100 before assembly. In the preferred approach, the conductors 30 and 34 are affixed before assembly by silver soldering.

The feedthrough 90 has been constructed in the manner discussed and tested. Two such feedthroughs were cycled 20 times between ambient temperature and 4K without failure.

The embodiments of FIGS. 3 and 5 are most suited to the situation wherein the thermal conductors 30 and 34 are single metallic pieces. In another construction, the conductors 30 and 34 may be formed as an array of braided or bundled smaller strands. For example, in the one approach the conductors 30 and 34 can be single metallic pieces of a diameter 0.25 centimeters. In the other approach, the conductors 30 and 34 can be about 1–100, preferably about 20, metallic strands each of a diameter of 0.3 millimeters.

Figure 6:
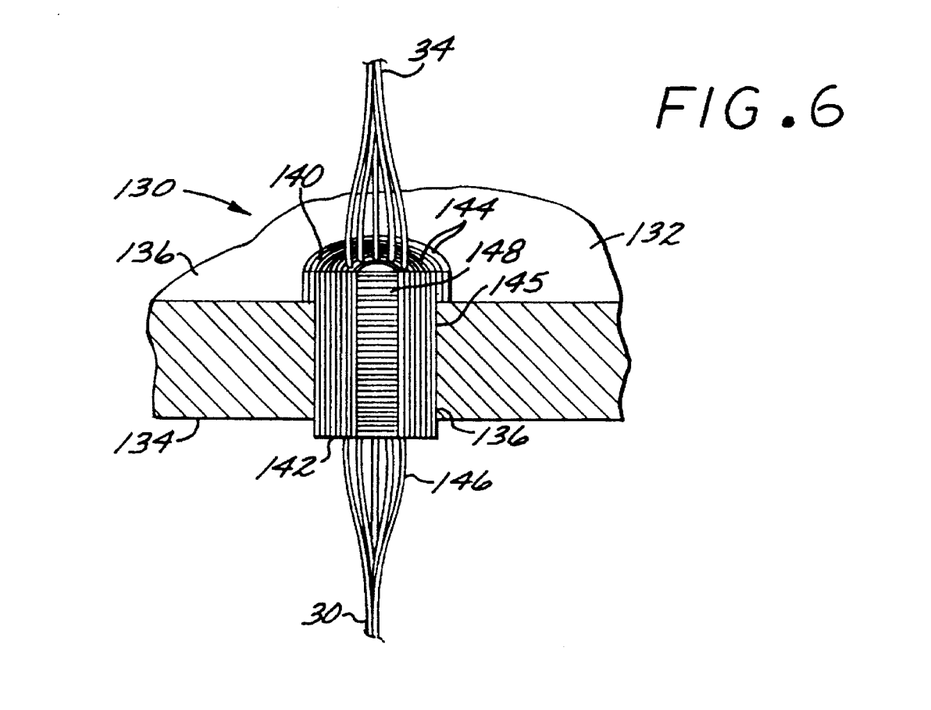
FIG. 6 is a side sectional view of a third embodiment of a thermal feedthrough.

The embodiment of FIG. 6 is particularly useful for the case where the thermal conductors 30 and 34 are formed as a number of individual conductors, either bundled or braided. The smaller size of the individual wires lessens the effects of strain caused by differential thermal contraction upon cooling to cryogenic temperature. A feedthrough 190 includes a fiber-reinforced plastic plate 132, preferably made of the same material as the plates 42 and 92. The plate 132 has a first surface 134 and a second surface 136. A bore 138 extends through the plate 132 from the first surface 134 to the second surface 136.

A plug 140 is formed as a roll 142 of individual turns 144 of a cured and hardened prepreg material. The plug is formed and then machined as necessary to fit within the bore 138 of the plate 132, and affixed within the bore 138 with an adhesive 145. The continuous thermal conductor 30, 34 is made of a plurality of individual strands 146. The individual metallic strands 146 are interleafed between the turns 144 of the roll 142. Since the individual strands 146 are quite small in size, the difference in absolute dimensional changes induced by thermal expansion differences between the plate and the plug is quite small. The cured and hardened prepreg material has some inherent compliancy that can accommodate this small absolute dimensional change. Stated alternatively, the thermal expansion dimensional changes which can otherwise lead to leaks through the feedthrough after temperature changes during service are spatially diffused sufficiently that the structure accommodates the changes and no leaks occur.

The plug 140 is manufactured by placing a strip of partially cured (B-stage cured) fiberglass prepreg material onto a surface. The prepreg material is soft and can be formed in this state. A cylindrical form 148 is placed at one end, and the strands 146 are placed at positions along the length of the strip crossing the strip. The strip 1s rolled onto the form 148 in a Jelly-roll fashion, capturing the strands 146 between the various turns 144 of the roll 142 as it forms. As the rolling proceeds, all of the strands 146 are captured between the turns 144 of the roll 142.

The B-staged material of the roll 142 is cured in the normal fashion. The curing usually involves placing the roll 142 (including the captured strands 146 and the form 148) into an autoclave or a pressure bag within a furnace. As the curing proceeds, the pressure on the roll forces the strands 146 of metal to be pressed into the curing prepreg material. The fibers of the prepreg material tend to surround and support the metal strands 146 in the final product. The close contact of the prepreg material and the strands ensures an absence of a leak path, and the previously mentioned spatial diffusion of the thermal expansion displacements avoids the development of leaks during subsequent temperature excursions during service.

After the plug 140 is cured, it is machined as necessary along its outside dimensions to fit within the plate bore 138 as shown. The plug 140 is placed within the bore 138 and fixed into place with an adhesive such as an ambient-temperature curable epoxy. The seal between the plug 140 and the plate 132 is accomplished by standard techniques, because the thermal expansion of the cured epoxy of the plug 140 and the fiber-reinforced plastic of the plate 132 are comparable.

The structure of the feedthrough 130 has been constructed. Two samples were tested by cycling it 20 times between ambient temperature and 4K. There was no failure of the feedthrough.

Figure 7:
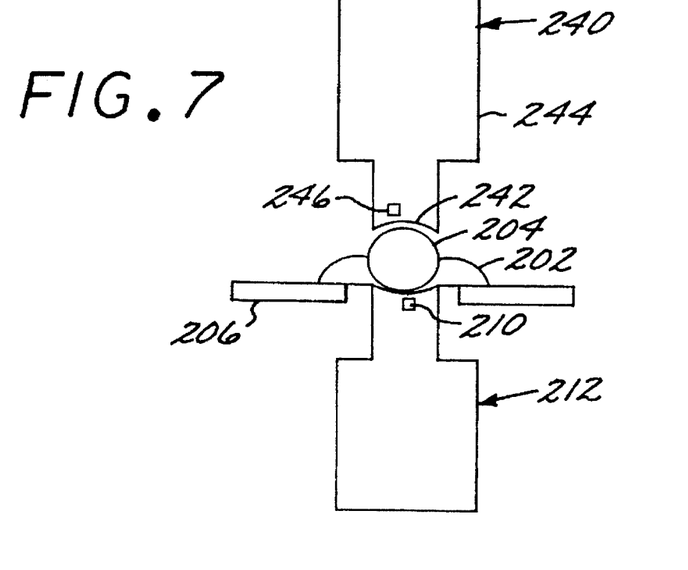
FIG. 7 is a schematic end elevational view of another embodiment of the biomagnetometer of the invention.

FIG. 7 illustrates another form of the invention. The vacuum enclosure 212, placed below the subject, is of the form illustrated and discussed in relation to FIGS. 1–6. A second portion of the biomagnetometer 208, including an upper vacuum enclosure 240, is placed above the subject. The upper vacuum enclosure 240 has a concavely downwardly curved second wall 242 and a first wall 244. A pickup coil 246 is positioned within the vacuum enclosure 240 and adjacent to the concavely curved second wall 242. The remainder of the structure for the vacuum enclosure 240 including the SQUID, the electrical connections and feedthrough, the thermal conductor and feedthrough, cooling reservoir, electronics, and computer, are the same as discussed previously for the portion of the apparatus including the vacuum enclosure 212, but are not shown again in FIG. 7 for clarity of illustration. Alternatively, the upper vacuum enclosure 240 may utilize conventional vacuum enclosure design, since it is located above the subject. Together, the arrays of pickup coils located within the two vacuum enclosures 212 and 240 give nearly full head coverage for a subject in a reclining position. Such coverage has not heretofore been available.

Figure 8A:
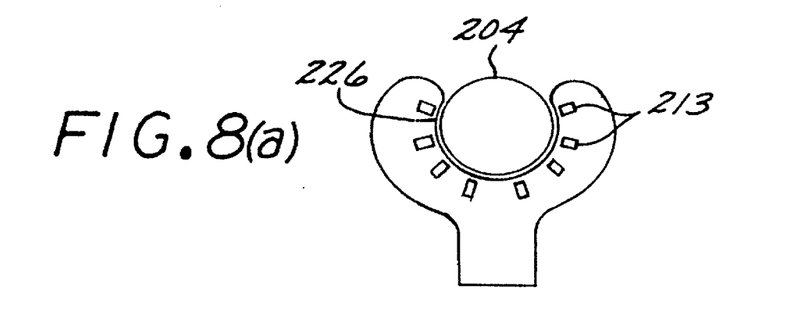
Figure 8B:
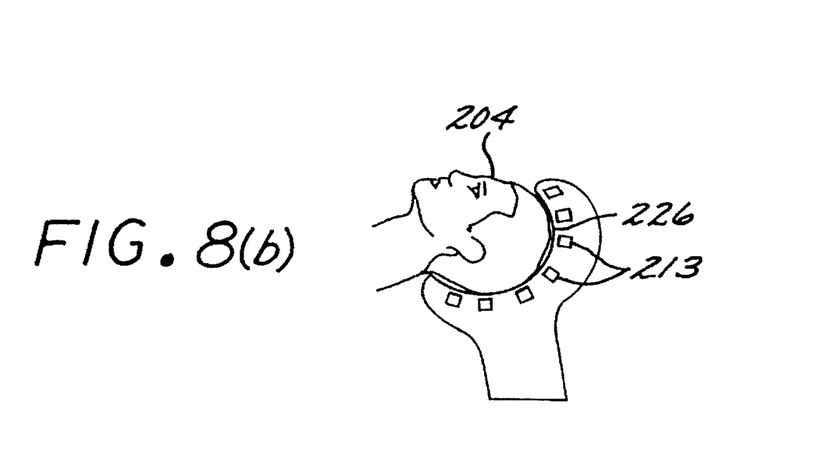

Another arrangement is shown in FIG. 8. Here, the first wall 226 is configured as a helmet to achieve coverage of a large portion of the head of the subject.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A biomagnetometer, comprising:
   a magnetic field sensor, including
      a magnetic field pickup coil, and
      an electrical current detector in electrical communication with the pickup coil;
   a vented reservoir of liquefied gas;
   an uninterrupted solid thermal conductor extending from the magnetic field sensor to the interior of the reservoir;
   a vacuum-tight thermal feedthrough by which the solid thermal conductor passes between the exterior and the interior of the reservoir;
   a vacuum-tight enclosure surrounding the magnetic field sensor, the reservoir, the solid thermal conductor, and the vacuum-tight thermal feedthrough, the enclosure having a wall including a concavely upwardly curved first wall portion with the magnetic field pickup coil located adjacent to the first wall portion;
   an electronic circuit, at least a portion of the electronic circuit being located exterior to the enclosure;
   an electrical lead extending from the electrical current detector to the portion of the electronic circuit located exterior to the enclosure;
   a vacuum-tight electrical feedthrough by which the electrical lead passes between the interior and the exterior of the enclosure;
   a second enclosure having a concavely downwardly curved second wall, the downwardly curved second wall being positioned in facing relation to the upwardly curved first wall portion;
   a second magnetic field sensor, including
      a second magnetic field pickup coil located within the second enclosure adjacent to the curved second wall, and
      a second electrical current detector in electrical communication with the second pickup coil; and
   means for cooling the second magnetic field sensor.

2. The biomagnetometer of claim 1, further including a plurality of additional magnetic field sensors located within the enclosure.

3. The biomagnetometer of claim 1, further including means for evacuating the interior of the enclosure.

4. The biomagnetometer of claim 1, wherein at least a portion of the solid conductor is a solid wire.

5. The biomagnetometer of claim 1, wherein at least a portion of the solid conductor is a multistrand array of wires.

6. A biomagnetometer, comprising:
a first dewar assembly comprising
  a vacuum-tight first enclosure having a concavely upwardly curved first wall,
  a first pickup coil within the first enclosure located adjacent the concavely upwardly curved first wall,
  a first detector of an electrical current in electrical communication with the first pickup coil, and
  means for cooling the first pickup coil and the first detector; and
a second dewar assembly comprising
  a vacuum-tight second enclosure having a concavely downwardly curved second wall, the downwardly curved second wall being positioned in facing relation to the upwardly curved first wall,
  a second pickup coil within the second enclosure located adjacent the concavely downwardly curved second wall,
  a second detector of an electrical current in electrical communication with the second pickup coil, and
  means for cooling the second pickup coil and the second detector.

7. The biomagnetometer of claim 6, wherein the first wall of the first dewar assembly and the second wall of the second dewar assembly are separated by a distance sufficiently large to receive a human head therebetween.

8. The biomagnetometer of claim 6, wherein the first means for cooling includes
  a vented reservoir of liquefied gas located within the first enclosure,
  a solid thermal conductor extending from the first pickup coil to the reservoir, and
  a vacuum-tight thermal feedthrough by which the solid thermal conductor passes between the exterior and the interior of the reservoir.

9. A biomagnetometer, comprising:
means for sensing a magnetic field, the means for sensing including
  an array of magnetic field pickup coils, and
  an array of detectors of small electrical currents flowing in the respective pickup coils;
a vacuum-tight enclosure surrounding the means for sensing and having a concavely downwardly curve first wall;
a vented reservoir of cryogenic liquid located within the enclosure;
a solid thermal conductor extending from the means for sensing into the reservoir; and
a vacuum-tight thermal feedthrough for the solid thermal conductor extending through a wall of the reservoir between the exterior of the reservoir and the interior of the reservoir;
second means for sensing a magnetic field, the second means for sensing including
  a second array of magnetic field pickup coils, and
  a second array of detectors of small electrical currents flowing in the respective pickup coils;
a second enclosure surrounding the second means for sensing, the second enclosure having a concavely downwardly curved second wall positioned in facing relation to the first wall; and
means for cooling the second means for sensing.

10. The biomagnetometer of claim 9, wherein the array of magnetic field pickup coils is located adjacent to the concavely upwardly curved first wall.

11. The biomagnetometer of claim 9, wherein the first wall and the second wall are separated by a distance sufficiently large to receive a human head therebetween.

12. The biomagnetometer of claim 9, wherein the vacuum-tight thermal feedthrough comprises
  a fiber-reinforced plastic plate having a first surface and a second surface, and further having a threaded plate bore therethrough;
  a threaded bolt made of a metallic alloy and engaged to the threaded plate bore, the bolt having an interior bolt bore therethrough;
  a first metallic thermal conductor extending through the interior of the interior bolt bore;
  a layer of a first adhesive between the threads of the bolt and the bore of the plate;
  a first retainer engaged between the bolt and the plate adjacent to the first surface of the plate;
  a second retainer engaged between the bolt and the plate adjacent to the second surface of the plate, the second retainer including
    a volume of a second adhesive contacting the second surface of the plate, and
    a nut threadably engaged to the bolt, the first retainer, the second retainer, and the bolt cooperating to place the bolt in tension and the plate in compression;
  a second metallic thermal conductor affixed to the first metallic conductor at a first end thereof; and
  a third metallic thermal conductor affixed to the first metallic conductor at a second end thereof.

13. The biomagnetometer of claim 9, wherein the vacuum-tight thermal feedthrough comprises
  a fiber-reinforced plastic plate having a first surface and a second surface, and further having a plate bore therethrough; and
  a plug sized to fit within the plate bore and affixed into the plate bore, the plug comprising:
    a length of a cured fiber-reinforced composite material wound onto a cylindrical nonmetallic form into a generally cylindrical, multiturn, Jelly roll coil, with the cylindrical axis of the coil generally perpendicular to the surfaces of the plate, and
    at least two thermally conductive wires penetrating between the turns of the coil and through the length of the cylindrical coil generally parallel to a cylindrical axis of the coil.

14. A biomagnetometer, comprising:
means for sensing a magnetic field, the means for sensing including
  an array of magnetic field pickup coils, and
  an array of detectors of small electrical currents flowing in the respective pickup coils;
a vacuum-tight enclosure surrounding the means for sensing;
a vented reservoir of cryogenic liquid located within the enclosure;
a solid thermal conductor extending from the means for sensing into the reservoir;
a vacuum-tight thermal feedthrough for the solid thermal conductor extending through a wall of the reservoir between the exterior of the reservoir and the interior of the reservoir;
a fiber-reinforced plastic plate having a first surface and a second surface, and further having a plate bore therethrough, the plate bore having a first diameter over a first portion of its length and a second, larger diameter over a second portion of its length adjacent to the second surface;

a metallic conductive plug positioned within the plate bore and having a first diameter over a first portion of its length and a second, larger diameter over a second portion of its length, the first portion of the plate bore being sufficiently large to receive the first portion of the plug therein with an interference fit, and the second portion of the plate bore being sufficiently large to receive the second portion of the plug therein, the plate being in radial compression in the region of the plate bore; and an adhesive seal between the plate and the plug.

* * * * *